(12) United States Patent
Monif (10) Patent No.: US 7,476,530 B1
(45) Date of Patent: Jan. 13, 2009

(54) MYCOBACTERIUM AVIUM SUBSPECIES PARATUBERCULOSIS ORAL VACCINE AND METHODS

(75) Inventor: Gilles R. G. Monif, Omaha, NE (US)

(73) Assignee: Infectious Diseases Incorporated, Bellevue, NE (US)

( * ) Notice: Subject to any disclaimer, the term of this patent is extended or adjusted under 35 U.S.C. 154(b) by 0 days.

(21) Appl. No.: 11/070,983

(22) Filed: Mar. 3, 2005

Related U.S. Application Data (62) Division of application No. 10/665,233, filed on Sep. 17, 2003, now abandoned.

(51) Int. Cl.
*A61K 39/04* (2006.01)
(52) U.S. Cl. .................. 435/252.3; 435/6; 435/7.21; 424/248.1; 424/200.1; 424/190.1; 424/93.2
(58) Field of Classification Search .................. 424/9.1, 424/9.2, 184.1, 234.1, 248.1; 435/243, 252.1, 435/253.1, 440
See application file for complete search history.

(56) References Cited

U.S. PATENT DOCUMENTS

| | | | | |
|---|---|---|---|---|
| 5,628,994 | A * | 5/1997 | Kaper et al. | 424/93.2 |
| 5,861,163 | A * | 1/1999 | Kim et al. | 424/260.1 |
| 6,277,580 | B1 * | 8/2001 | Ellingson et al. | 435/6 |
| 6,833,135 | B1 * | 12/2004 | Frazao Moniz Pereira et al. | 424/248.1 |
| 2002/0064861 | A1 * | 5/2002 | Barletta et al. | 435/252.3 |
| 2003/0044431 | A1 * | 3/2003 | Schurig et al. | 424/252.1 |
| 2003/0092080 | A1 * | 5/2003 | Braun et al. | 435/7.21 |
| 2004/0109875 | A1 * | 6/2004 | Kernodle et al. | 424/200.1 |
| 2005/0058663 | A1 * | 3/2005 | Monif | 424/200.1 |
| 2005/0232937 | A1 * | 10/2005 | Willemsen et al. | 424/190.1 |
| 2005/0250120 | A1 * | 11/2005 | Cole et al. | 435/6 |
| 2007/0134274 | A1 * | 6/2007 | Talaat | 424/248.1 |
| 2007/0134708 | A1 * | 6/2007 | Talaat et al. | 435/6 |
| 2007/0202131 | A1 * | 8/2007 | Jacobs et al. | 424/248.1 |

OTHER PUBLICATIONS

Secott, Te et al, Infection and Immunity, vol. 70(5), pp. 2670-2675, May 2002. Fibronectin attachment Protein is necessary for Efficient attachment and invasion of epithelial cells by Mycobacterium avium subsp. paratuberculosis.*

Secott et al , Infection and Immunity, Apr. 2001, vol. 69(4), pp. 2075-2082, Fibronectin attachment protein homologue mediates fibronectin binding by Mycobacterium avium subsp. paratuberculosis.*

Harris, N. Beth et al, Clinical Microbiology Reviews, Jul. 2001, vol. 14(3), pp. 489-512, Mycobacterium avium subsp. paratuberculosis in Veterinary Medicine.*

(Continued)

*Primary Examiner*—Shanon A. Foley
*Assistant Examiner*—Ginny Portner (57) ABSTRACT

A method of using selective binding properties of killed and live isolates of *Mycobacterium avium* subspecies paratuberculosis (Map) to gastrointestinal tract mucosa is described which permits:

selecting as a killed Map test candidate for oral administration a strain of Map which will have greater organismal attachment; and selecting as a live Map test candidate for oral administration a live strain of Map whose virulence had been significantly reduced and which exhibits a diminished ability to bind to gastrointestinal mucosa The method also includes preservation of binding ability of Map isolates after inhibition of organism replication or virulence reduction.

18 Claims, 8 Drawing Sheets

ATTACHMENT OF DIFFERENT STRAINS TO THE INTESTINE: DATA FROM 2 ANIMALS

OTHER PUBLICATIONS

Sangari, Felix J et al, Infection and Immunity, vol. 69(3), pp. 1515-1520, May 2001, Mycobacterium avium Invades the instestinal mucosa primarily by interacting with Enterocytes.*

Experimental Oral Infection of Calves with Mycobacterium Johnei by Gilmoure et al.; J. Comp. Path. 1965, vol. 75.

Production of -interferon by peripheral blood mononuclear cells: an important diagnostic tool for detection of subclinical paratuberculosis by Stabel; J. Vet Diagn invest 8:345-350 (1996).

Experimental infectin of weaner sheep with S strain Mycobacterium avium subsp. paratuberculosis by Reddacliff et al.; Veterinary Microbiology, vol. 96, Issue 3, Oct. 30, 2003, pp. 247-258.

Attachment of Mycobacterium avium subspecies paratuberculosis to Bovine Intestinal Organ Cultures: Method Development and Strain Differences, Shleig et al., 2005. (Not Prior Art).

Schleig P. M et al: Veterinary Microbiology 108 : 271-279 , 2005.

* cited by examiner

Figure 1

ATTACHMENT OF DIFFERENT STRAINS TO THE INTESTINE: DATA FROM 2 ANIMALS

Attachment of M. paratuberculosis

M. paratuberculosis Strain

MYCOBACTERIUM AVIUM SUBSPECIES PARATUBERCULOSIS ORAL VACCINE AND METHODS

This application is a division of utility application Ser. No. 10/665,233 filed Sep. 17, 2003 and now abandoned.

BACKGROUND OF THE INVENTION (1) Field of the Invention

The present invention relates generally to vaccines and, more particularly, to a method and vaccine for inducing mucosal immunity and a method for selecting the vaccine candidate.

(2) Description of the Prior Art

Both killed and live vaccines have been administered by parenteral injection to achieve systemic humoral and cellular immunity.

For mycobacteria and, in particular, *Mycobacterium avium* subspecies paratuberculosis (MAP), commitment to parenteral administration has been based on the relative efficacy of bacillus Calmette-Guerin (BCG) vaccine against *Mycobacterium tuberculosis* in human beings.

Basic similarities exist between *Mycobacterium tuberculosis* and *Mycobacterium avium* subspecies paratuberculosis. The portal of infection for *M. tuberculosis* is the lung; its site of pathology is the lung. For MAP, its portal of infection is the gastrointestinal tract which is also its organ of manifested disease.

What has not been computed into prior MAP vaccine development is the fact that upper lobe disease is a metastatic site of disease resulting from hematogenous dissemination. Inhalation acquisition of *M. tuberculosis* primarily involves the superior segments of the lower lobes or the right middle lobe of the lung. Gohn complexes occur in the lymphatic sites of the primary infection. If host T-cell mediated and humoral immunity do not arrest organismal replication at site of initial infection, the organism enters into the blood stream and seeks out optimal conditions for future replication, more specifically, metastatic progressive upper lobe disease. Upper lobe disease is the consequence of bacillemia and metastatic implantation, which accounts for the success of IgG immunoglobulins and systemic T-cell immunity in precluding or arresting the development of metastatic disease in the upper lobes.

For *Mycobacterium avium* subspecies paratuberculosis (MAP), the portal of infection is die gastrointestinal tract. The target organ is the gastrointestinal disease Gastrointestinal histopathology does not require a phase of systemic dissemination. Hematogenous dissemination is a late phenomena and not a major factor in determining the consequences of disease for the animal.

Mucosal local humoral immunity is mediated primarily by the IgA class of immunoglobulins. IgG specific antibodies do function in a secondary manner within mucosal immunity. What parenteral killed and live MAP vaccines have demonstrated is that IgG specific antibodies, in concert with transported T-cell response can impact locally on the magnitude of fecal shedding and systemically prolong the interim between established mucosal infection and Johne's disease. The importance of local immunity for mycobacteria is inferred by the observation that immunization of guinea pigs with vaccines directed against hsp60 of *Mycobacterium tuberculosis* did not preclude the development of necrotizing bronchiolitis when a hsp60 heat shock protein of *M. tuberculosis* was applied to the traditional portal of infection, but the animals were protected systemically.

Drawing parallels between *Mycobacterium tuberculosis* and MAP, it is presumed that some cows with either Phase I and II infection may self-cure. Work done in conjunction with the Department of Pathobiology at the University of Florida, College of Veterinary Medicine has suggested that self-cure may occur in cows with Phase III disease. Serial blood samples were obtained from a cow with culture and serologically documented Johne's disease in order to collect high titer antibody titered serum. Prior to euthanasia, the animal cease having diarrhea and began gaining weight. At necropsy, the gastrointestinal tract was basically normal. A rare histological section demonstrated MAP.

Disease, as opposed to infection, is often a titration between infectious inoculum, organismal virulence and host immune response. If the inoculum dose is controlled and organismal virulence is altered, it is reasonable to assume that the probability of host immunity prevailing is enhanced. With a live oral vaccine, prolonged immunological memory is more likely despite infection containment.

Attempts to induce local immunity with heat-killed vaccine strains have been unsuccessful.

The failure of both live and killed, parentally administered, MAP vaccines to preclude ultimate disease turns the focus of investigation to the importance of local immunity induction within the target organ. A need exists for a vaccine that is effective in preventing disease at the portal of infection/target organ.

SUMMARY OF THE INVENTION

The present invention is directed toward a method of orally immunizing a host animal against a gastrointestinal or enteric, mucosally invasive organism, specifically *Mycobacterium avium* subspecies paratuberculosis (MAP). The method steps include providing an enteric, mucosally-adherent, non-systemically invasive, *Mycobacterium avium* subspecies paratuberculosis organism and orally administering the MAP organism to a host organism in an immunizing dose and manner.

The present invention is also directed toward a method of generating a gastrointestinal, mucosally adherent, non-systemically invasive, live mucosal vaccine organism. The method of generating the vaccine organism includes selecting one or more mucosal adherent organism strains based on desired binding affinity to an animal species' gastrointestinal tract; serially passaging the at least one strain in culture sufficient to significantly alter genomic expression; monitoring the passages for adherence to the mucosa of interest; demonstrating in-vivo alteration of the pathogenicity, including the mucosal histopathogenicity, and non-systemic invasiveness of the at least one passaged strain; and testing for the ability of the at least one passaged strain to confer protection against mucosal challenge by wild MAP strains.

The present invention is further directed towards a mucosal vaccine against an oral *Mycobacterium avium* subspecies paratuberculosis, consisting of a mucosally adherent, non-invasive, *Mycobacterium avium* subspecies paratuberculosis organism and a pharmaceutically acceptable carrier.

Accordingly, one aspect of the present invention is to provide a method of orally immunizing a host organism against a gastrointestinal or enteric, mucosally invasive organism, specifically *Mycobacterium avium* subspecies paratuberculosis, the method steps including providing an enteric, mucosally-adherent, non-systemically invasive, *Mycobacterium avium* subspecies paratuberculosis organism and orally administering the MAP organism to a host organism in an immunizing dose and manner.

Another aspect of the present invention is to provide a method of generating a gastrointestinal, mucosally adherent, non-invasive, live mucosal vaccine organism, including selecting at least one mucosa-adherent organism strain based on desired binding affinity to an animal species' gastrointestinal tract; serially passaging the at least one strain in culture sufficient to alter genomic expression; monitoring the passages for adherence to the mucosa of interest; demonstrating in-vivo alteration of mucosal histopathogenicity, and absence of systemic invasiveness of the at least one passaged strain; and testing for the ability of the at least one passaged strain to confer protection against mucosal challenge.

Still another aspect of the present invention is to provide an orally administered mucosal vaccine against *Mycobacterium avium* subspecies paratuberculosis, consisting of a mucosally adherent, non-systemically invasive, *Mycobacterium avium* subspecies paratuberculosis organism and a pharmaceutically acceptable carrier.

These and other aspects of the present invention will become apparent to those skilled in the art after a reading of the following description of the preferred embodiment when considered with the drawings.

DETAILED DESCRIPTION OF THE PREFERRED EMBODIMENTS

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms. Referring to the figures in general, the graphs are for the purpose of demonstrating the characteristics of a preferred embodiment of the invention and are not intended to limit the invention thereto.

The present invention is directed toward a method of orally immunizing a host organism against a gastrointestinal or enteric, mucosally invasive organism, specifically *Mycobacterium avium* subspecies paratuberculosis (MAP). The method steps include providing an enteric, mucosally-adherent, non-systemically invasive, *Mycobacterium avium* subspecies paratuberculosis organism and orally administering the MAP organism to a host organism in an immunizing dose and manner.

The MAP organism preferably stimulates a Th1-type response and elicits IgA secretion and a CMI response. The MAP is preferably a viable organism, although a killed organism may be used. In the case of a killed organism, the organism is killed using non-protein denaturing means, such as lethal irradiation, such as UV-irradiation, gamma-irradiation, particle-beam irradiation, and the like. The MAP may also be a recombinant organism carrying immunogenic genes from other pathogens.

The present invention is also directed toward a method of generating a gastrointestinal, mucosally adherent, non-invasive, live mucosal vaccine organism. The method of generating the vaccine organism includes selecting at least one mucosa-adherent organism strain based on desired binding affinity to an animal species' gastrointestinal tract; serially passaging the at least one strain in culture sufficient to alter genomic expression; monitoring the passages for adherence to the mucosa of interest; demonstrating in-vivo attenuation of the pathogenicity, including the mucosal histopathogenicity, and invasiveness of the at least one passaged strain; and testing for the ability of the at least one passaged strain to confer protection against mucosal challenge.

The animal species for which a vaccine according to the present invention can be developed and administered include all those that can be infected through the gastrointestinal mucosa, more specifically all those that can be infected by MAP through the gastrointestinal mucosa.

The method of generating a vaccine can also include the use of mutagens in culture to increase the mutation frequency of the at least one strain. Additionally, the method can also include monitoring for pathogenicity and/or invasiveness in cell culture prior to in vivo testing.

The present invention is further directed towards a mucosal vaccine against an oral *Mycobacterium avium* subspecies paratuberculosis, consisting of a mucosally adherent, non-invasive, *Mycobacterium avium* subspecies paratuberculosis organism and a pharmaceutically acceptable carrier.

The MAP organism preferably stimulates a Th1-type response and elicits IgA secretion and a CMI response. The MAP is preferably a viable organism, although a killed organism may be used. In the case of a killed organism, the organism is killed using non-protein denaturing means, such as lethal irradiation, such as UV-irradiation, gamma-irradiation, particle-beam irradiation, and the like. The MAP may also be a recombinant organism carrying immunogenic genes from other pathogens.

The present invention includes a method of orally immunizing a host organism against a gastrointestinal, or enteric, mucosally invasive organism, specifically *Mycobacterium avium* subspecies paratuberculosis (MAP). The MAP organism is preferably one that targets the intestinal mucosa as the target organ. The immunization method steps include providing an enteric, mucosally-adherent, non-systemically invasive, *Mycobacterium avium* subspecies paratuberculosis organism and orally administering the MAP organism to a host organism in an immunizing dose and manner.

The vaccine organism will preferably have the following characteristics in order to achieve immunization according to the present invention: a) retained mucosal adherence to MAP receptor sites within the GI tract; b) organism tissue invasion is limited to the mucosal portion of GI tract; c) non-systemically invasive; d) mucosal and serum cytokine pattern and character of lesions induced differ from those created by wild strains; e) mucosal cytokine pattern and histopathology characteristics indicative of a Th1 response; and f) the immunity elicited, either alone or in conjunction with parenteral MAP sub-fraction vaccines, will withstand wild-type strain challenge.

Retained Mucosal Adherence to Map Receptor Sites within the GI Tract.

Mucosal adherence is a prerequisite for mucosal internalization. This fact is substantiated by the failed attempts to induce immunity using heat-killed MAP orally administered vaccines. If the attachment piece is damaged or non-existent, such as by heat-denaturation, internalization will be significantly impaired.

Organism Tissue Invasion is Limited to the Mucosal Portion of GI Tract—Non-Systemic Invasiveness.

Although the vaccine organism is non-systemically invasive, the vaccine organism can invade the mucosa of the GI tract. An oral live MAP vaccine needs to achieve limited mucosal penetration to elicit long-term immunological memory. With other mycobacterium infections, like that produced by *M. tuberculosis*, recovery from disease is not totally predicated on total organismal drug eradication. Ultimate organismal control is achieved by the host immune system. Drug therapy serves primarily to reduce organismal mass to quantum governable by host immunity. Immune deficiency syndromes have demonstrated that viable organism can persist in a static relationship with prior disease site. By genetic modification of virulence and control of immunizing dose, oral MAP vaccines can engender a sufficiently effective Th1 response to achieve arrestment of organismal replication within the target organ and yet stimulate long term immunological memory.

Mucosal and Serum Cytokine Pattern and Character of Lesions Induced Differ from those Created by Wild Strains.

With Th2 immune response induction, intra-macrophage replication of MAP predominates and live organisms are disseminated by macrophages within portions of the reticuloendothelial system, the so-called lepromatous lesion phase, which correlates with MAP serological responsiveness. The initial phase of MAP invasion stimulates a predominantly Th1 response which histologically is characterized by presence of lymphocytes as opposed to a Th2 characteristic lesion in which epitheloid cells/macrophages predominate. MAP organisms are comparatively rare within a Th1 correlating lesion in contrast to their relative abundance within macrophages when cytokine pattern are consistent with a progressive Th2 response, Mucosal Cytokine Pattern and Histopathology Characteristics Indicative of a Th1 Response.

Th1 and Th2 responsiveness to MAP experimental infection tend to have characteristic predominance of a specific type of histological lesion as discussed above.

The MAP organism preferably stimulates a Th1-type response and elicits IgA secretion and a cell-mediated immune response. The vaccine organism will also preferably cause organismal histopathology in the host GI tract characteristic of a Th1 response.

The Immunity Elicited, Either Alone or in Conjunction with Parenteral Map SUB-Fraction Vaccines, will Withstand Wild-Type Strain Challenge.

Local immunity can be potentially overwhelmed by progressively increasing the size of the challenge dose. Parenteral administration of killed MAP vaccines contribute to local mucosal immunity as demonstrated by prolongation of time to disease and reduced fecal organismal shedding in vaccinated cows. Once the upper limit of wild MAP challenge is established, a decision as to the need or desirability of a combined oral and parenteral MAP vaccination approach to infection containment can be assessed.

The present invention is also directed toward a method of generating a gastrointestinal, mucosally adherent, non-invasive, live mucosal vaccine organism. The method of generating the vaccine organism includes selecting at least one mucosa-adherent organism strain based on desired binding affinity to an animal species' gastrointestinal tract; serially passaging the at least one strain in culture sufficient to alter genomic expression; monitoring the passages for adherence to the mucosa of interest; demonstrating in-vivo attenuation of the pathogenicity, including the mucosal histopathogenicity, and invasiveness of the at least one passaged strain; and testing for the ability of the at least one passaged strain to confer protection against mucosal challenge.

The method of generating a vaccine can also include the use of mutagens in culture to increase the mutation frequency of the at least one strain.

Work done by the inventor has shown that specific receptors for MAP exist within the bovine gastrointestinal tract, that they involve fibronectin, that they are relatively uniformly distributed within the bovine gastrointestinal, that different strains of MAP have different binding affinities, and that persistence of mucosal binding can be preserved despite attenuation of selected oral vaccine candidates.

Basic Methodology:

MAP Strains: Five strains of MAP were tested in the pending publication entitled "Attachment of *Mycobacterium avium* subspecies paratuberculosis to bovine intestinal organ culture: Method development and strain differences." Veterinary Microbiology 2005 108:271-279: ATTC49164 (Strain A; Isolate from a patient with Crohn's disease), ATCC43015 (Strain B; Isolate from a patient with Crohn's disease), ATCC19698 (Strain C—isolate from a cow with naturally acquired paratuberculosis, MAP 728 (Strain B—a passage 10 of a clinical isolate) and MAP 7283 (Strain F—a passage 543 of a clinical isolate).

Culture Methodology: A bacteriological loop was used to transfer the organisms to a 50 ml cell culture flask containing 30 ml of 7H9 broth with glycerol (Remel, Lenexa, Kans.). S35 Methionine (Trans35S-Label; ICN Biomedical, INC. Irvine, Calif.) was added at a concentration of 8 uCi per ml. All flasks were labeled appropriately and placed in a 37° C., 5% CO2 incubator for three weeks.

Calves and Animal Husbandry

Experimental Animals: Animal use protocols were reviewed and approved by the University of Florida Institutional Animal Care and Use Committee in accordance with the Guide for the Care and Use of Laboratory Animals. Four male Holstein calves approximately 2 to 4 days old were obtained from a farm in North Florida. Calves were obtained as needed and were housed overnight in the food animal barn at the College of Veterinary Medicine where they were supplied with bedding and water. Calves were sacrificed via electrocution using standard practices in the College of Veterinary Medicine necropsy suite. Two calves were used in the attachment assays.

Necropsy and Tissue Preparation: After the calves were sacrificed, each was placed on the necropsy table, the abdomen was opened, and full section strips of the bovine intestine were obtained aseptically through standard necropsy techniques. The intestines were washed with sterile saline to remove fecal material and placed in whirl bags on ice for transport to the laboratory. Strips were dampened with saline to prevent drying. In the laboratory, the strips were washed again with saline to remove any remaining feces, the strips were cut to the proper size, placed in labeled petri dishes, a Teflon insert with a rectangle cut taken from the center was placed in each petri dish to hold the tissue flat. Organ cultures were established from the lower-ileum, mid-ileum, upper-ileum, mid-jejunum, and the colon.

Attachment Procedure: The radiolabeled strains of MAP (stains A, B, C, E, and F) were scraped from each of the 50 ml cell culture flasks, concentrated by centrifugation, and the pellets washed three times with sterile saline. Pellets were then suspended in 15 ml of RPMI-1640 with L-Glutamine (BioWhittaker, Walkersville, Md.) and 10% fetal calf serum and sonicated for two minutes to break up clumps. After sonication, the organism were pushed through a 2L gauge needle to break up the remaining clumps and then the concentrated organisms were added to 110 ml of RPMI with 10% fetal calf serum to total a total volume of 125 ml. A sample of each strain of organism was taken and quantitative cultures done by serial dilution and plating on 7H11 agar (Remel, Lenexa, Kans.). An additional sample was taken to determine file disintegrations per minute (DPM) for the same size sample as that used for the quantitative cultures. This allowed us to determine the labeling efficiency for each strain of MAP. Twenty-five ml of RPMI solution containing the radiolabelled organisms was placed in each of the five petri dishes containing the different gut sections. This was done for all MAP strains in respectively labeled petri dishes with the gut sections. The petri dishes were then placed in a 37° C., 5% CO2 incubator on an adjustable reciprocating orbital shaker for three hours. At the end of the incubation period, the strips of the intestine were washed three times with saline removing any unattached organisms. Three punches from each strip were taken from the center of each strip using a 6 mm Miltex dermal biopsy punch to ensure that a constant size volume was taken and that edge effects were avoided. Punches were placed in labeled scintillation vials containing 3 ml of Wallac Optisolv solubilizer and vials were placed in the 37° C., 5% CO2 incubator overnight. Scintillation fluid (Wallac Optiphase Highsafe 3) was added to the scintillation vials and they were placed in scintillation racks for counting. The amounts of the organisms that bound to the intestine organ cultures were quantitated by scintillation counting to detect the S35 methionine for 30 minutes per sample. DPMs per standard area were recorded and converted to CFUs by calculating the labeling efficiency of each strain of MAP on the day of the experiment and converting the DPM to CFU via multiplication of the ratio of CFU/DPM.

A full-length strip of tissue was cut from the remaining tissue, rolled so that the lumen could be fully visualized, placed in tissue cassettes, preserved in 10% buffered formalin, and prepared for histological sections via standard methods.

Fibronectin Treatment Attachment Procedure: Because we were mainly interested in how clinical isolates could be affected by coating with fibronectin, and we could not perform these assays using all strains of MAP, we used only three strains of MAP for these experiments. We used strains B. E, and F because strain B comes from a Crohn's disease patient, and strains E and F are low and high in vitro passage clinical isolates from cattle. The same procedure was followed as described previously except after the last wash of the different strains, the organisms were each split into two aliquots. One aliquot of each strain was suspended in 800 ul phosphate buffered saline (PBS) and the other half was suspended in 800 ul 0.1% fibronectin solution from bovine plasma (Sigma-Aldrich Co., St Louis, Mo.). These solutions were then sonicated as described previously and incubated for 1 hour at 37° C. in a 5% CO2 incubator.

Histology: The tissues were processed for paraffin embedding and sections cut for H&E, Brenn and Brown, and Acid Fast stains. These sections were examined by light microscopy to determine whether or not the tissue appeared normal and to localize the organisms in relation to tissue landmarks.

Statistical Analysis: Statistical analyses to detect differences in the attachment of the different strains of MAP to the different sections of the intestine as well as fibronectin treated versus non-fibronectin treated MAP were analyzed by a two-way analysis of variance (ANOVA). Strains (ATCC49164, ATCC43015, ATCC19698, UF7283B, and UF7283) attachments to the following five different regions were studied. Strains with fibronectin treatment (ATCC43015, UF7283B, and UF7283) versus the control of non-fibronectin organisms in PBS (ATCC43015, UF7283B, and UF7283) were analyzed. When ANOVA indicated a significant difference among groups, a Bonfererroni/Dunn multiple mean comparison was also performed to determine which groups were different. Statistics were performed using Microsoft Excel software (Microsoft, Redmond, Wash.) and Statview software (SAS institute, Cary, N.C.).

Demonstration of Map Receptors within the Bovine Gastrointestinal Tract:

Results for this attachment study can be seen in FIGS. 1 through 8. The labeling efficiencies for the different strains of the MAP varied among strains. By this it is meant that the CFU/DPM ratio determined through plating each strain compared with the DPMs given for each strain varied (i.e., some strains incorporated more radioactive material then others and some grew more than others). The labeling efficiency for strains B, C, E, and F were all approximately equal (2-10 CFU/DPM), while stain A was quite a bit different labeling at approximately 97 CFU/DPM. The estimated CFU was determined by taking the recorded DPM for each punch and multiplying it by the appropriate ratio. This gives the approximate CFU that attached. All data was converted from DPMs to estimated CFUs and then transformed to parametric data by taking the natural logarithm (LN) of each value. This transformation was used because the organisms grow in a geometric progression as they divide, and this is best represented by natural logarithms of the data. Statistical analyses and graphs were done on the LN transformed data.

Figure 1:
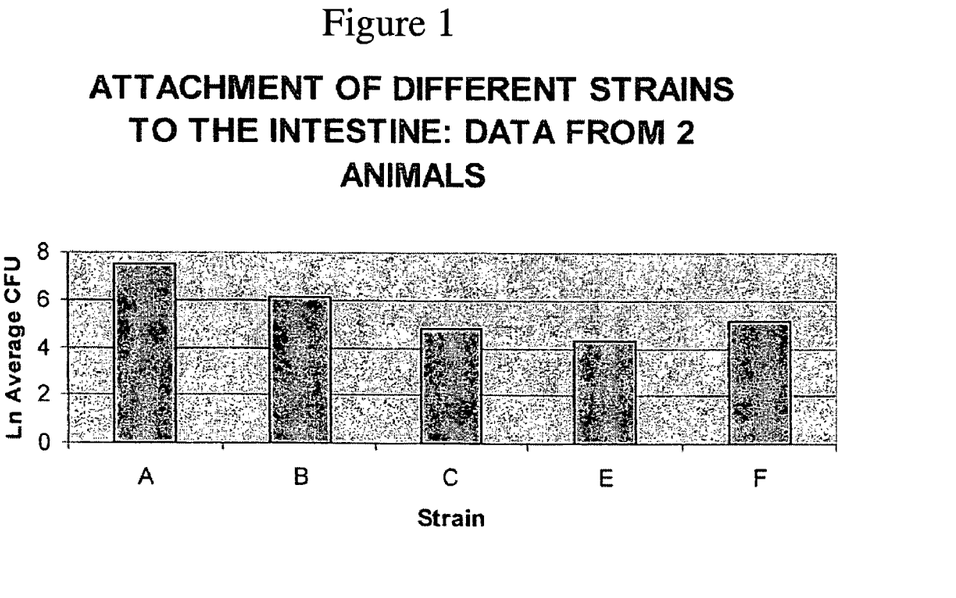
FIG. 1 is a graph showing divergent intestinal attachment affinity of 5 different MAP strains.

FIG. 1 is a graph showing divergent intestinal attachment affinity of 5 different MAP strains: (A=ATCC49164 isolate from a Crohn's disease patient, B=ATCC43015 isolate from a Crohn's disease patient, C=ATCC19698 isolate from the feces of a cow with naturally acquired MAP, E=UF7283B Low Pass Isolate, and F=strain E after modification of genetic expression.) to the intestine. All are statistically different from each other (P<0001) except strains C and F (P=0.2184).

Figure 2:
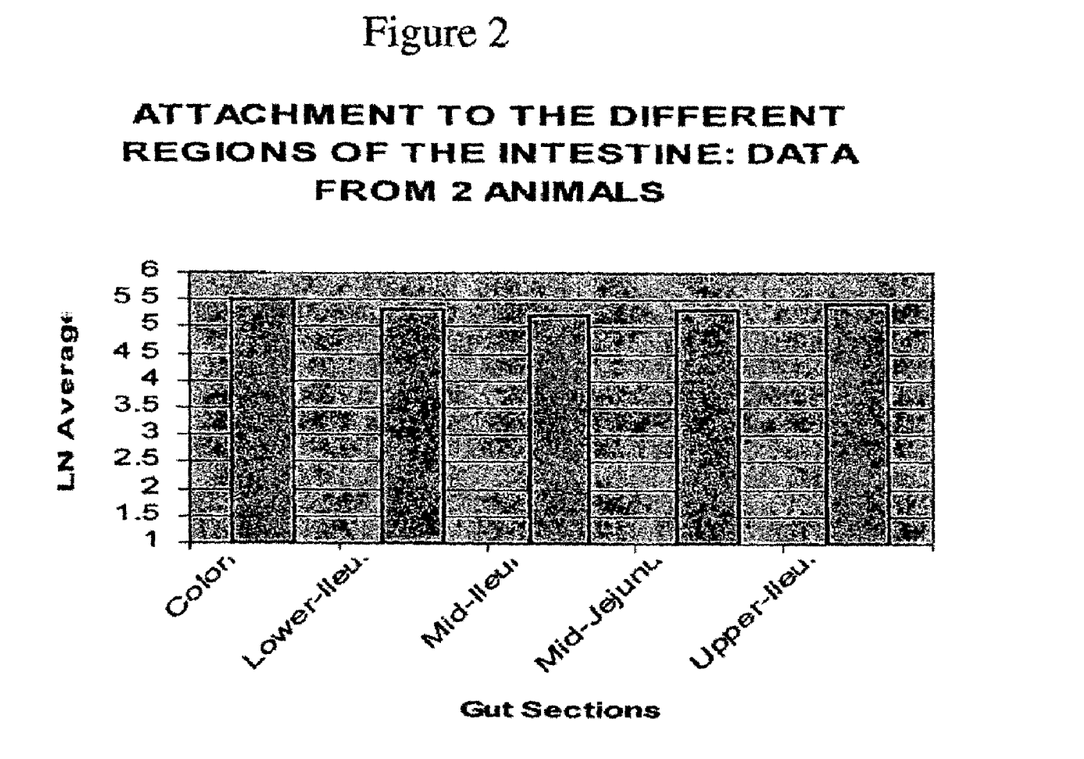
FIG. 2 is a graph relatively equivalent intestinal attachment of 5 different MAP strains within the gastrointestinal tract.

FIG. 2 is a graph demonstrating intestinal attachment of 5 different MAP strains to different regions of the bovine intestinal epithelium.

Figure 3:
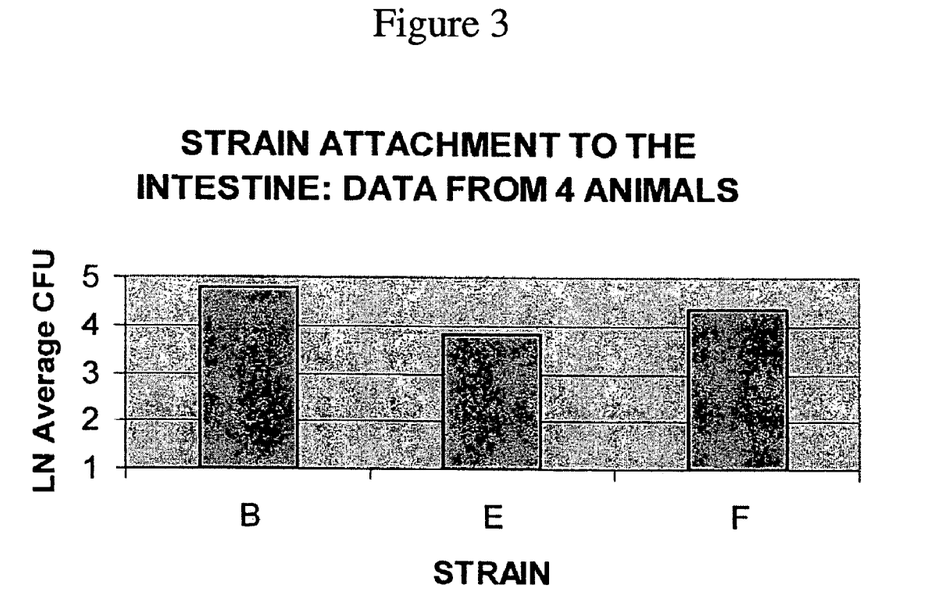
FIG. 3 is a graph showing the effect of passage on intestinal attachment affinity of 3 different MAP strains.

FIG. 3 is a graph showing the effect of passage on intestinal attachment affinity of 3 different MAP strains (B=ATCC43015 isolate from a Crohn's disease patient. E=low passage of an oral vaccine candidate. F=strain E after modification of genetic expression.) Strains are statistically different from each other (P=2.3210×10$^{-5}$)

Figure 4:
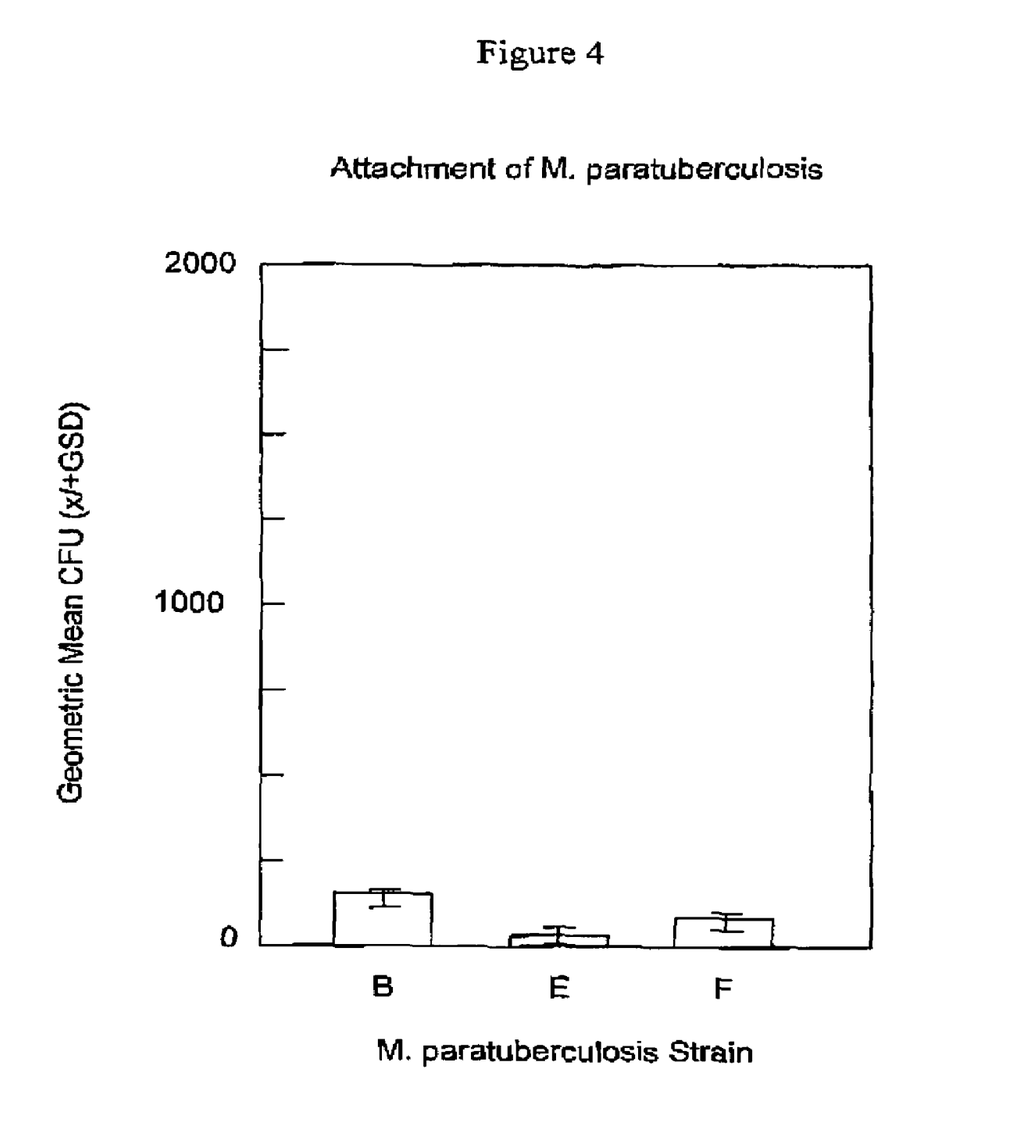
FIG. 4 is a graph showing the effect of passage on intestinal attachment location of 3 additional different MAP strains.

FIG. 4 is a graph showing the attachment of different strains of MAP to the bovine intestinal epithelium organ cultures. (B=ATCC43015 isolate from a Crohn's disease patient, E=UF7283B Low Pass Isolate, and F=strain B after modification of geneic expression.) to the 5 different regions of the intestine. Strains are not statistically different from each other (P=0.989144).

Figure 5:
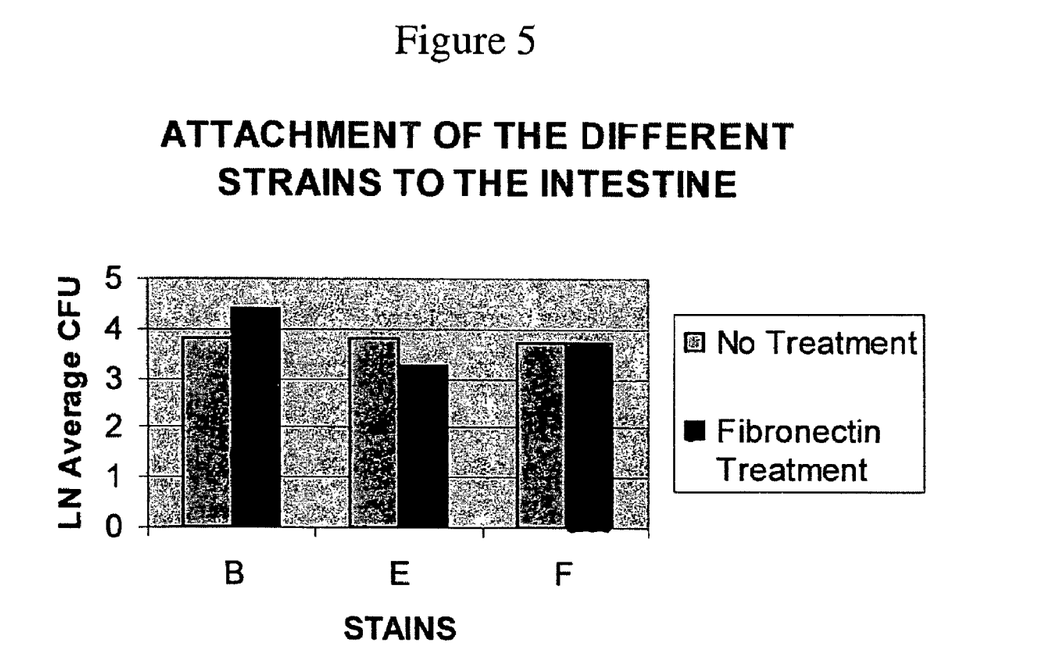
FIG. 5 is a graph showing the effect of fibronectin treatment on intestinal attachment affinity of 3 different MAP strains.

FIG. 5 is a graph showing the effect of fibronectin treatment on intestinal attachment affinity of 3 different MAP strains (B=ATCC43015 isolate from a Crohn's disease patient, E=UF7283B Low Pass Isolate of an oral vaccine candidate. F=Strain E after modification of genetic expression. Fibronectin treatment is on the right versus no treatment on the left. Strains B and F show no statistical difference in attachment between treatments (P=0.771063 and P=0.331623) respectively. Strain E is significantly different (P=0.009406).

Figure 6:
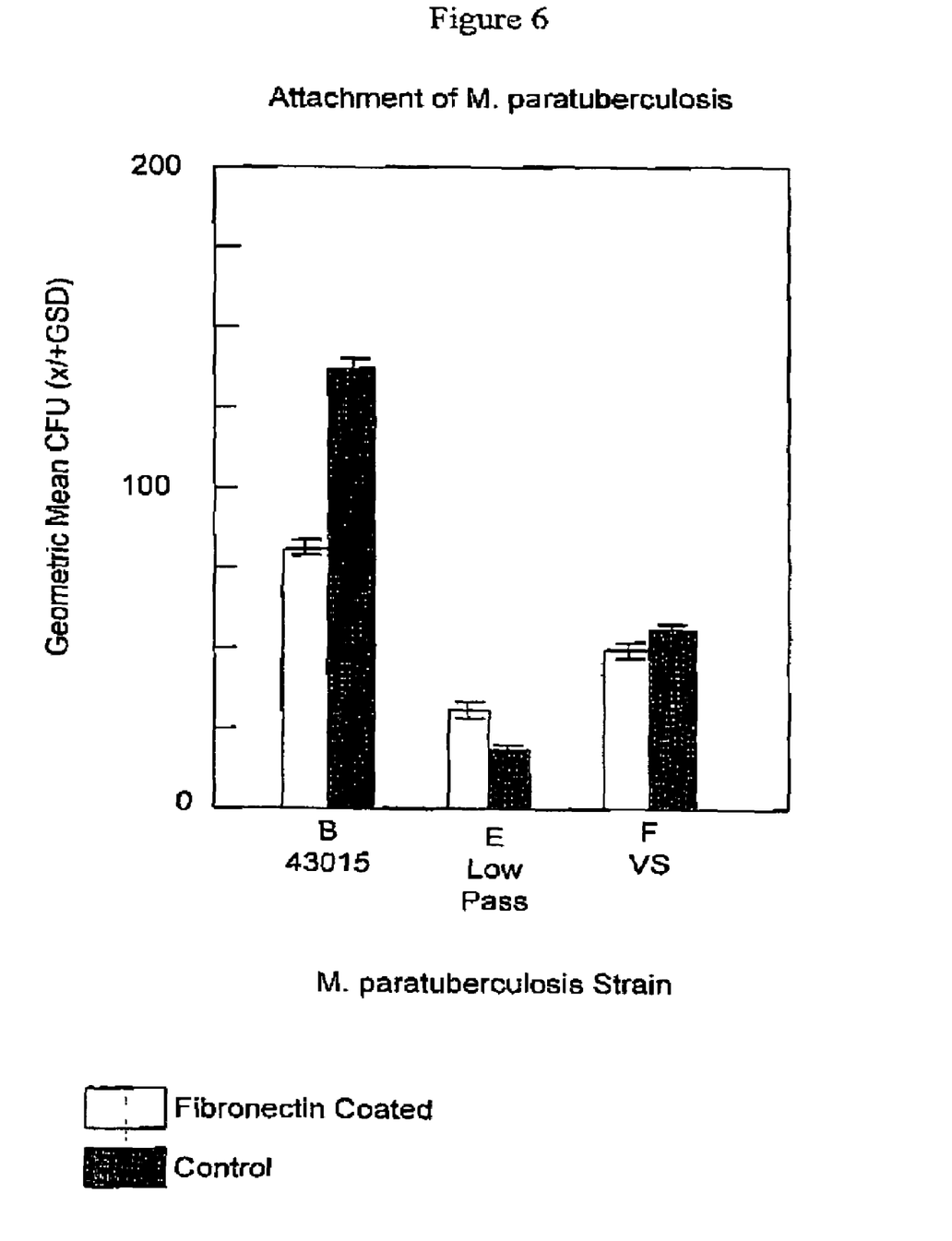
FIG. 6 is a graph showing the effect of fibronectin treatment on divergent intestinal attachment location of 3 different MAP strains.

FIG. 6 is a graph showing the effect of fibronectin treatment on divergent intestinal attachment location of 3 different MAP strains. B=ATCC43015. E-low passage of an oral vaccine candidate. F=strain E after modification of genetic expression. Strains did not show a significant difference in attachment to different regions of the bovine gastrointestinal tract (Strain B P=0.745992; Strain E P=0.362609; and Strain F P=0.766836). Fibronectin treated samples versus untreated samples showed a significant difference in the mid-ileum (P=0.0087) and lower-ileum (P=0.0096).

Figure 7:
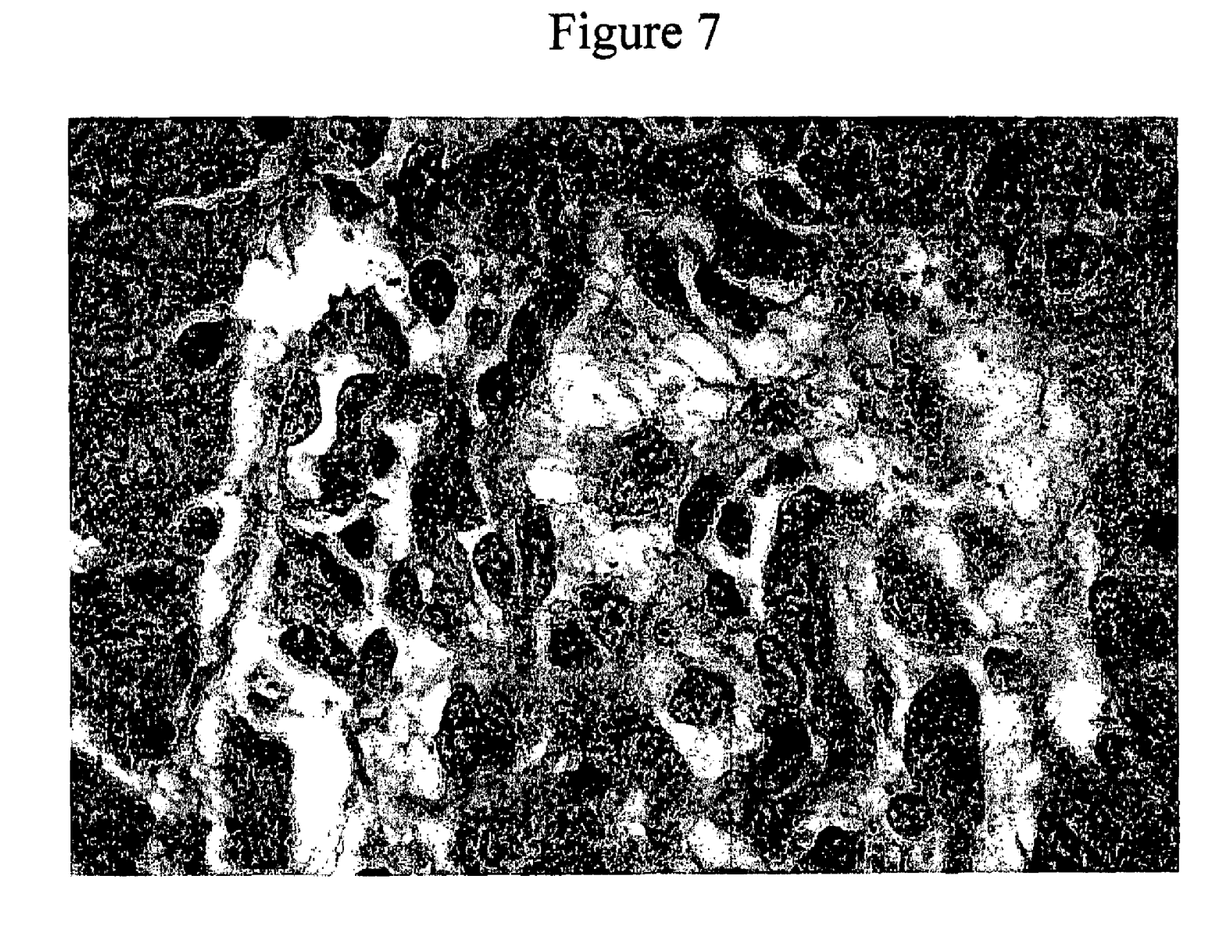
FIG. 7 is a histological photomicrograph of a sample of tissue from the colon confirming mucosal presence of MAP.

FIG. 7 is a histological photomicrograph of a sample of tissue from the colon confirming mucosal presence of MAP.

Figure 8:
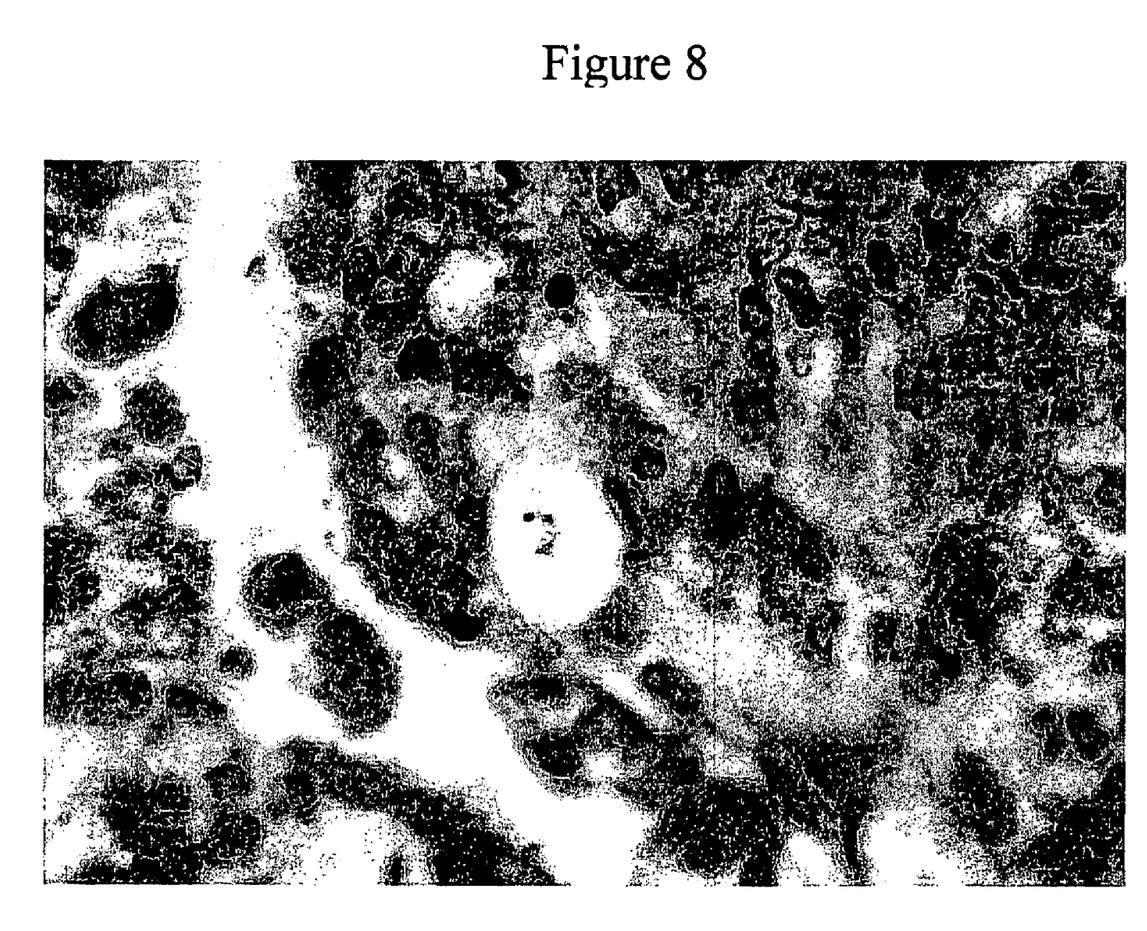
FIG. 8 is a histological photomicrograph of a sample of tissue from the lower ileum confirming the presence of MAP within a goblet cell.

FIG. 8 is a histological photomicrograph of a sample of tissue from the lower ileum confirming the presence of MAP within a goblet cell.

Characterization of Map Binding Site with Field and Attenuated Strains:

FIGS. 5 and 6 present data from fibronectin treatment study. Fibronectin coating of the organisms did not effect the attachment of the two high passage strains of MAP, but did affect the binding of the low passage clinical isolate. The fibronectin treatment decreased the attachment of the low passage clinical isolate to the calf gut epithelium (FIG. 6). Fibronectin treatment decreased attachment only in the mid ileum and the lower ileum.

Distribution of Map Receptor Sites within the Bovine Gastrointestinal Tract.

The log CFU (colony forming unit) for the five strains is listed in FIG. 1. The CFU/DPM colony forming unit/disintegration per minute) ratio was basically different for each strain. Strain C attached to the same degree as strain F. For strains, B, C, E and F, the labeling efficiency was approximately 2-10 CFU/DPM/ (FIG. 2). Strain A, the inactivated oral vaccine candidate was statistically different from the other strains studied (P<0.00001). Its CFU/DPM ratio was 97.

The live attenuated oral vaccine candidates exhibited relatively constant mucosal binding despite serial in vitro passage in excess of 500 culture passages (FIG. 2). Early passage strain had a CFU/DPM ratio of 2 whereas that long-term passage strain had a CFU/DPM of 6. There was no significant difference in the region of the gastrointestinal tract to which MAP attached (P=0.5214) as shown in FIG. 2.

There was no statistical difference in the five intestinal sites studied. However, slightly more organismal attachment occurred in the terminal ileum and colon.

Differences in Binding Affinities of Map Isolates:

Results for this attachment study can be seen in FIGS. 1 through 8. The labeling efficiencies for the different strains of the MAP varied among strains. By this it is meant that the CFU/DPM ratio determined through plating each strain compared with the DPMs given for each strain varied (i.e., some strains incorporated more radioactive material then others and some grew more than others). The labeling efficiency for strains B, C, E, and F were all approximately equal (2-10 CFU/DPM), while stain A was quite a bit different labeling at approximately 97 CFU/DPM. The estimated CFU was determined by taking the recorded DPM for each punch and multiplying it by the appropriate ratio. This gives the approximate CFU that attached. All data was converted from DPMs to estimated CFUs and then transformed to parametric data by taking the natural logarithm (LN) of each value. This transformation was used because the organisms grow in a geometric progression as they divide, and this is best represented by natural logarithms of the data. Statistical analyses and graphs were done on the LN transformed data.

In each graph, LN of average estimated CFU is presented along the y-axis and MAP strain or gut section is presented along the x-axis. In FIG. 1 (data from experiment with 2 animals and no fibronectin treatment) the only comparison among strains that is not significantly different is between strain C and F. In FIG. 2 (same experiment) there is no significant difference in the region to which the organisms attached. FIGS. 3 and 4 presents combined data from all four animals in which no fibronectin treatment is used are shown. All three strains of MAP attach differently from each other (p<0.001), with the low passage clinical isolate attaching less than the other two strains. However, there is not a significant difference in which section of the intestine to which the organisms attach (FIG. 4).

FIGS. 7 and 8 are pictures taken of tissue that was embedded in paraffin and sectioned for acid fast staining. FIG. 8 illustrates the normal morphology of the lower ileum, while 7 illustrates that of the colon. FIGS. 7 and 8 show the organisms in a goblet cell.

Certain modifications and improvements will occur to those skilled in the art upon a reading of the foregoing description. All modifications and improvements have been deleted herein for the sake of conciseness and readability but are properly within the scope of the following claims.

I claim:

1. A method for selecting mucosa adherent strains of *Mycobacterium avium* subspecies paratuberculosis (MAP) in the development of an oral MAP vaccine, the steps comprising:
    a) screening and identifying a live wild MAP isolate with binding affinity to calf gastrointestinal mucosa in-vitro,
    b) altering the live wild MAP isolate to achieve a mucosal adherent, altered MAP isolate by a method selected from the group consisting of: serial passage of the isolate in-vitro, serial passage of the isolate in-vitro in the presence of mutagens, serial passage in a host animal, and genetic modification of virulence to effect genomic expression,
    c) re-screening and selecting an altered MAP isolate retaining the ability to bind to gastrointestinal mucosa,
    d) demonstrating the selected altered MAP isolate is attenuated relative to the live wild MAP isolate in-vivo,
    e) selecting an altered MAP isolate for oral administration that stimulates a predominant TH-1 immune response, the TH-1 immune response differing from the live wild MAP isolate, said altered MAP isolate having an adherence colony forming unit (CFU) to disintegrations per minute (DPM) ratio (CFU/DPM) that is statistically significant higher when compared with other altered isolates,
    f) orally administering to a host animal the selected altered MAP isolate that elicits a predominant TH-1 immune response in a dosage and frequency necessary to illicit a local MAP TH-1 response, along with a specific IgG immunoglobulin, a specific IgA immunoglobulin or cell-mediated immunity, g) testing the altered MAP strains for the ability to preclude wild-type MAP from adhering to host animal gastrointestinal mucosa against mucosal challenge with wild-type MAP in a host animal.

2. The method of claim 1, wherein the altering step b) is a method selected from the group consisting of: serial passage of the isolate in-vitro, serial passage of the isolate in-vitro in the presence of mutagens, and genetic modification of virulence.

3. The method of claim 2, wherein the altered MAP is a live recombinant carrying immunogenic genetic components.

4. The method of claim 1, wherein the re-screening and selecting step c) comprises the step of monitoring mucosa adherence in vitro.

5. The method of claim 1, wherein the altered MAP administered in step f) is a live isolate.

6. The method of claim 5, wherein the altered MAP is a live recombinant MAP carrying immunogenic genetic components.

7. The method of claim 1, wherein the altered MAP administered in step f) is viable.

8. The method of claim 1, wherein the orally administered composition of step f) comprises a pharmaceutical carrier.

9. The method of claim 1, wherein the host animal of step g) is selected from the group consisting of bovine host animals, cows, calves, Holstein calves, and animals included in animal husbandry.

10. A method for selecting enteric, mucosa adherent strains of *Mycobacterium avium* subspecies paratuberculosis (MAP) or enteric, mucosal adherent, non-systemically invasive enteric organism, in the development of an oral, killed MAP vaccine, the steps comprising:
  a) screening and identifying live wild MAP isolates with high affinity to calf gastrointestinal mucosa in-vitro,
  b) killing the identified MAP isolate by any one or more methods selected from the group consisting of: irradiation, UV-irradiation, gamma-irradiation and particle-beam irradiation,
  c) re-screening and selecting killed MAP isolates retaining the ability to bind to gastrointestinal mucosa,
  d) stimulating an immune response by orally administering to a host animal the selected killed MAP isolate to stimulate a Th1-type response and/or stimulate MAP specific IgA immunoglobulin production and cell-mediated immune response, and
  e) testing the ability of the killed MAP strain to prevent oral challenge with wild-type MAP isolated from establishing persistent infection and/or disease within the gastrointestinal tract of said host animal.

11. The method of claim 10, wherein the killing step b) does not result in protein denaturation of surface proteins of the identified MAP isolate.

12. The method of claim 10, wherein the killed MAP gastrointestinal mucosa binding of step
  d) is primarily fibronectin binding activity.

13. The method of claim 12, wherein the fibronectin binding activity is tested in-vitro or in-vivo.

14. The method of claim 13, wherein said in-vitro testing is carried out with cell culture of mucosa derived epithelial cells or gastrointestinal mucosa to which live MAP strains adhere.

15. The method of claim 10, wherein the stimulating an immune response step d) further comprises the step of administering the killed MAP orally or orally and parenterally.

16. The method of claim 10, wherein the orally administering step d) comprises administering the killed MAP isolate together with a pharmaceutical carrier.

17. The method of claim 10, wherein the host animal of step e) is selected from the group consisting of bovine host animals, cows, calves, Holstein calves, and animals included in animal husbandry.

18. The method of claim 10, further comprising the steps of a) through e) being carried out with a gastrointestinal or enteric, mucosal invasive organism to obtain an additional enteric, mucosal, adherent, non-systemically invasive organism.

* * * * *